United States Patent
Zhu et al.

(10) Patent No.: US 8,749,579 B2
(45) Date of Patent: Jun. 10, 2014

(54) PIXEL-FEATURE HYBRID FUSION FOR PET/CT IMAGES

(75) Inventors: Yang-Ming Zhu, Solon, OH (US); Charles A. Nortmann, Richmond Heights, OH (US)

(73) Assignee: Koninklijke Philips N.V., Eindhoven (NL)

( * ) Notice: Subject to any disclaimer, the term of this patent is extended or adjusted under 35 U.S.C. 154(b) by 353 days.

(21) Appl. No.: 13/145,135

(22) PCT Filed: Dec. 23, 2009

(86) PCT No.: PCT/IB2009/055952
§ 371 (c)(1),
(2), (4) Date: Jul. 19, 2011

(87) PCT Pub. No.: WO2010/084390
PCT Pub. Date: Jul. 29, 2010

(65) Prior Publication Data
US 2012/0019548 A1     Jan. 26, 2012

Related U.S. Application Data

(60) Provisional application No. 61/146,331, filed on Jan. 22, 2009.

(51) Int. Cl.
*G09G 5/00* (2006.01)
(52) U.S. Cl.
USPC ........... 345/629; 345/589; 345/592; 345/634; 382/131; 382/132
(58) Field of Classification Search
None
See application file for complete search history.

(56) References Cited

U.S. PATENT DOCUMENTS

| | | | |
|---|---|---|---|
| 5,810,007 A | 9/1998 | Holupka et al. | |
| 6,466,224 B1 | 10/2002 | Nagata et al. | |
| 8,200,040 B2 * | 6/2012 | Pfister | 382/284 |
| 2005/0015004 A1 | 1/2005 | Hertel et al. | |
| 2007/0097143 A1 | 5/2007 | Ii et al. | |
| 2007/0160272 A1 | 7/2007 | Nagamine et al. | |
| 2008/0238947 A1 | 10/2008 | Keahey et al. | |

FOREIGN PATENT DOCUMENTS

| | | |
|---|---|---|
| EP | 1923838 A1 | 5/2008 |
| JP | 2001291091 A | 10/2001 |
| JP | 2003061956 A | 3/2003 |
| JP | 2006025448 A | 1/2006 |
| JP | 2007307125 A | 11/2007 |

OTHER PUBLICATIONS

Huang, G., et al.; Visual and infrared dual-band false color image fusion method motivated by Land's experiment; 2007; Optical Engineering; 46(2)027001-1-027001-10.

(Continued)

*Primary Examiner* — Antonio A Caschera

(57) ABSTRACT

An image display method comprises: color coding a second image respective to an intensity spectrum with a portion or portions of the intensity spectrum set to be transparent to generate a color coded second image; combining a first image and the color coded second image to generate a fused image; and displaying the fused image. An image display system comprises: an image generating module configured to generate an image by color coding an input image in accordance with a colormap assigning colors to intensities of an intensity spectrum; a colormap modifying module configured to select a portion of the intensity spectrum to be transparent; and a display configured to display the generated image.

26 Claims, 3 Drawing Sheets

(56) References Cited

OTHER PUBLICATIONS

Figure 1:
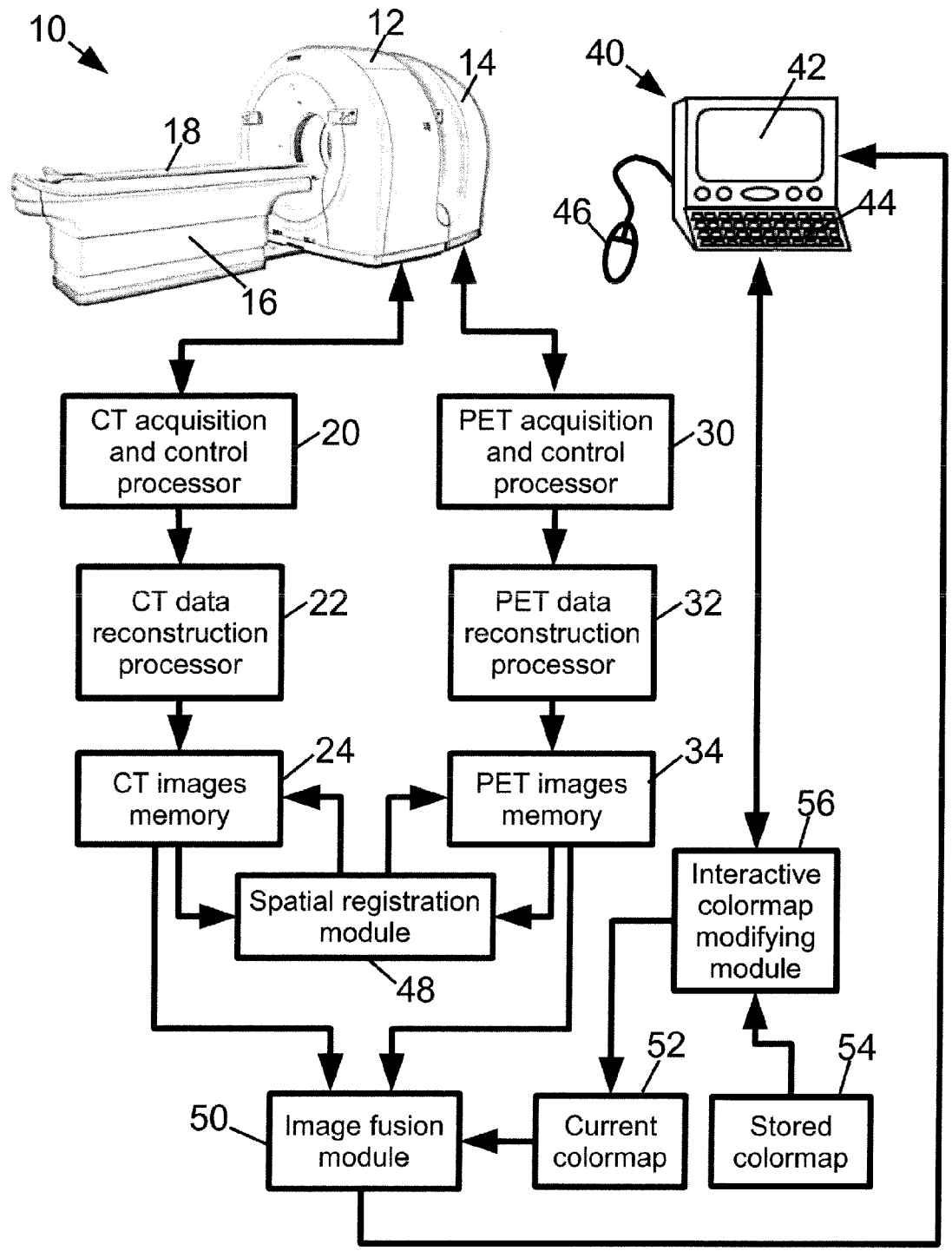

Rosset, A., et al.; Informatics in Radiology (infoRAD) Navigating the Fifth Dimension: Innovative Interface for Multidimensional Multimodality Image Navigation; 2006; Radiographics; http://radiographics.rsna.org/content/26/1/299.full.pdf+html>.

Russ, J. C.; Image Processing Handbook; Chapter 1: Acquiring Images-Color Imaging; 1999; 3rd Edition; CRC Press; pp. 32-37.

Aoki, H., et al.; PET Interpretation Support Method by Data Aggregation of Interpretation Information with Confirmed Diagnosis Stored in PET Image DB; 2008; Inst. of Electronics, Information & Communication Engineering (IEICE); 9 pages.

* cited by examiner

PIXEL-FEATURE HYBRID FUSION FOR PET/CT IMAGES

CROSS REFERENCE TO RELATED APPLICATIONS

This application claims the benefit of U.S. provisional application Ser. No. 61/146,331 filed Jan. 22, 2009, which is incorporated herein by reference.

The following relates to the multi-modality imaging arts, medical imaging arts, medical diagnostic arts, positron emission tomography (PET) imaging arts, computed tomography (CT) imaging arts, single photon emission computed tomography (SPECT) imaging arts, magnetic resonance (MR) imaging arts, ultrasound imaging arts, and related arts.

Multimodality imaging entails acquiring images of a subject using two or more different imaging modalities, such as CT and PET, or MR and PET, or CT and PET and MR, or so forth. The images of the different modalities may be acquired by a hybrid system such as a hybrid CT/PET system, or may be acquired by standalone systems such as a standalone CT system and a standalone PET system. Multimodality imaging can synergistically combine the strengths of the constituent imaging modalities to obtain more information than would be provided by any one single imaging modality operating alone.

One popular example of multimodality imaging is PET/CT, where the PET imaging provides substantial functional information such as metabolic activity information, while CT imaging provides substantial structural information. The synergistic combination enables functional information provided by PET to be placed into anatomical context provided by CT. Hybrid PET/CT imaging is useful, for example, in oncology where CT images can delineate a cancerous tumor and its surrounding anatomical neighborhood, while PET can provide information about metastasis, necrosis, or other functional aspects of the cancer.

Images from different modalities can be "combined" using a straightforward side-by-side comparison of the images. However, this approach requires the radiologist, physician, oncologist, or other medical specialist to synthesize the information from the two modalities in a wholly manual fashion. For example, the medical specialist is required to visually ascertain which regions of the images are spatially corresponding. Since the different imaging modalities provide different information and hence may "look different", it may be difficult for a medical specialist to correlate and synthesize side-by-side images of different modalities.

Accordingly, various image fusion display techniques have been developed. In these techniques, the images from the different modalities are overlaid or otherwise combined to generate a single "fused" image that carries information from both imaging modalities. Using PET/CT as an illustrative example, an overlay image fusion display shows the (principally anatomical) CT image in grayscale as an underlay image, and the (principally functional) PET image in pseudocolor as an overlay image. The colors assigned to the PET image pixels or voxels are selected from a colormap based on the pixel values. The underlay and overlay are blended together with an adjustable transparency. That is, the fused image is a weighted average of the underlay CT image and the overlay PET image. In some quantitative approaches, the adjustable transparency is controlled by a transparency factor denoted herein as $\alpha$, with the contribution from the underlay CT image weighted by $\alpha$ and the contribution from the overlay PET image weighted by $(1-\alpha)$, where $\alpha$ is between 0 and 1, inclusive. The transparency factor $\alpha$ is also sometimes referred to as the alpha value.

One problem with the image overlay technique is that it can distort information. For example, the visual system readily detects changes in color introduced by the PET overlay, but is not as strongly influenced by changes in the CT underlay grayscale intensity. As a result, the medical specialist may interpret color changes introduced by the PET overlay as dominant image features when, in fact, the perceived color change represents only a small change in PET image intensity.

Another problem with the image overlay technique is information overload. Image overlay is a form of pixel-level fusion. Image overlay does not discard any information. As a result, image overlay can present too much information to the medical specialist, making it difficult or impossible for the medical specialist to assimilate the fused information effectively. Image overlay also treats all pixels or voxels in the same way, which imposes substantial bandwidth on the human vision system.

One solution to this information overload problem is to extract the relevant features of one or both constituent images, and then fuse only the relevant features. For example, the tumor region can be identified and presented via image overlay, thus simplifying interpretation of the fused image. However, this approach is computationally intensive, and can introduce errors since it relies upon accurate automated determination of "medically relevant" features. The removal of information involved in isolating the relevant features can also remove too much information, so that insufficient context is provided to spatially relate features to anatomy.

The following provides new and improved apparatuses and methods which overcome the above-referenced problems and others.

In accordance with one disclosed aspect, an image display method comprises: color coding a second image respective to an intensity spectrum with a portion of the intensity spectrum set to be transparent to generate a color coded second image; combining a first image and the color coded second image to generate a fused image; and displaying the fused image.

In accordance with another disclosed aspect, an image display system comprises: an image generating module configured to generate an image by color coding an input image in accordance with a colormap assigning colors to intensities of an intensity spectrum; a colormap modifying module configured to select a portion of the intensity spectrum to be transparent; and a display configured to display the generated image.

In accordance with another disclosed aspect, a storage medium is disclosed which stores: a stored colormap assigning colors to intensities of an intensity spectrum; and instructions executable by a digital processing device to (i) color code an image in accordance with a current colormap and (ii) generate the current colormap by modifying the stored colormap.

In accordance with another disclosed aspect, an image display method comprises: displaying a structural image of a subject in grayscale; and color coding portions of the displayed structural image for which functional activity as determined from a functional image of the subject lies within one or more selected functional activity level ranges.

One advantage resides in providing more clinically informative multimodality image displays.

Another advantage resides in providing user-adjustable fused image displays.

Another advantage resides in providing user-adjustable highlighting in displayed clinical images.

Further advantages will be apparent to those of ordinary skill in the art upon reading and understand the following detailed description.

FIG. 1 diagrammatically illustrates a PET/CT imaging facility including processing components for spatially registering and fusing PET and CT images.

Figure 2:
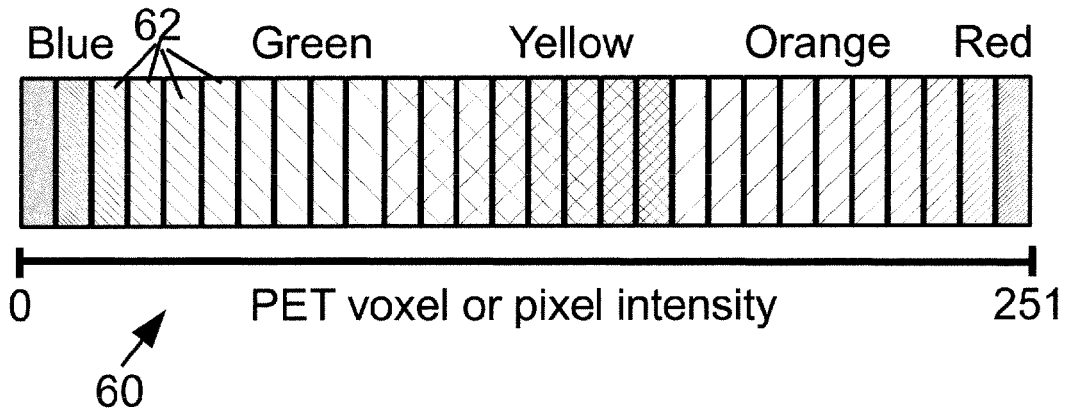

FIG. 2 diagrammatically illustrates a user-interactive colormap modification user interfacing display showing a representation of a stored colormap.

Figure 3:
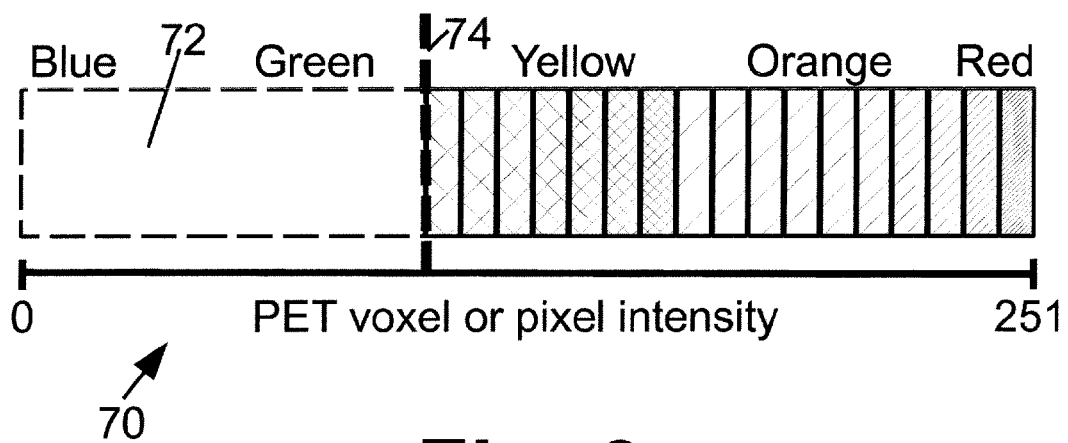

FIG. 3 diagrammatically illustrates a user-interactive colormap modification user interfacing display showing a representation of a first modification of the stored colormap.

Figure 4:
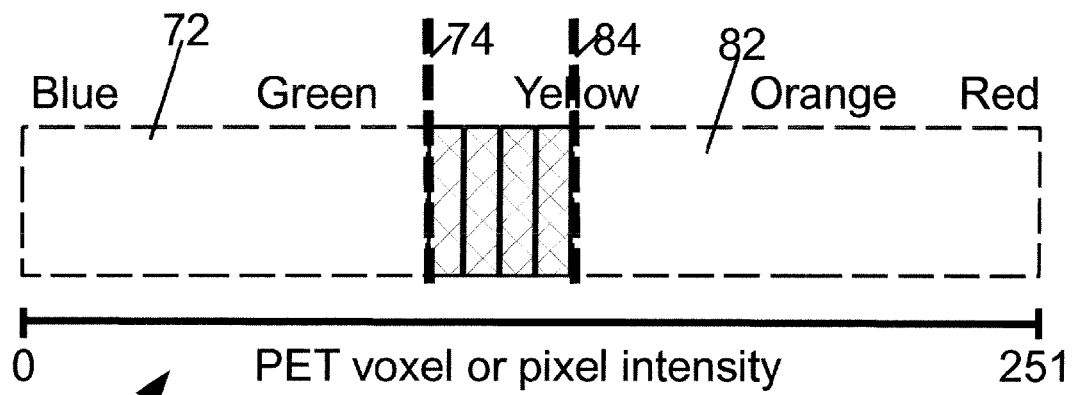

FIG. 4 diagrammatically illustrates a user-interactive colormap modification user interfacing display showing a representation of a second modification of the stored colormap.

Figure 5:
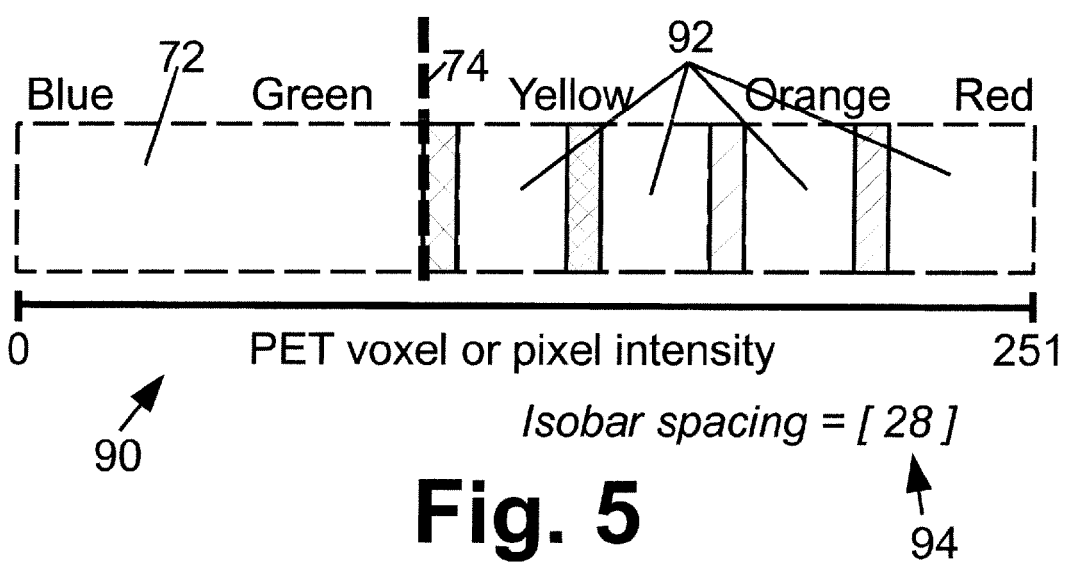

FIG. 5 diagrammatically illustrates a user-interactive colormap modification user interfacing display showing a representation of a third modification of the stored colormap.

With reference to FIG. 1, a multimodality imaging facility employs at least two different imaging modalities. In the illustrative examples set forth herein, the multi-modality imaging facility employs computed tomography (CT) and positron emission tomography (PET) imaging modalities using a hybrid PET/CT imaging system 10 that includes a CT gantry 12, a PET gantry 14, and a common subject support 16 for inserting a human subject, an animal subject, an inanimate subject such as a mummy or an archaeological artefact, a phantom, or so forth, into the CT gantry 12 for CT imaging or into the PET gantry 14 for PET imaging. The illustrative hybrid PET/CT imaging system 10 is a GEMINI™ PET/CT imaging system (available from Koninklijke Philips Electronics N.V., Eindhoven, The Netherlands) and is set forth herein as an illustrative example. Another hybrid PET/CT imaging system, or another hybrid imaging system such as a hybrid magnetic resonance (MR)/PET imaging system, a hybrid single photon emission computed tomography (SPECT)/PET imaging system, or so forth can be provided in addition to or in place of the illustrated GEMINI™ PET/CT imaging system 10. Moreover, multimodality imaging can instead or additionally be provided by one or more standalone imaging systems, such as a standalone CT scanner, a standalone PET scanner, a standalone MR scanner, a radiation gamma camera configured for SPECT imaging, or so forth. Still further, in some embodiments a single imaging instrument may be configured to provide multimodality imaging. For example, it is contemplated for the multimodality imaging system to include as few imaging instruments as a single gamma camera that is configurable to perform either SPECT or PET imaging.

For CT imaging, a movable pallet or bed 18 of the common subject support 16 is moved to place the subject to be imaged into a bore of the CT gantry 12, and a CT acquisition and control processor 20 controls an x-ray tube and cooperating x-ray detector array (components disposed in the CT gantry 12 and not visible in FIG. 1) to generate and acquire CT projection data that are reconstructed by a CT data reconstruction processor 22 to generate one or more CT images that are stored in a CT images memory 24. In similar fashion, for PET imaging the linearly translatable pallet or bed 18 is moved to place the subject into a bore of the PET gantry 14, and a PET acquisition and control processor 30 operates PET radiation detectors (disposed in the PET gantry 14 and not visible in FIG. 1) to acquire PET line-of-response data (optionally including time-of-flight localization) that are reconstructed by a PET data reconstruction processor 32 to generate one or more PET images that are stored in a PET images memory 34. In the case of PET imaging, a suitable positron-emitting radiopharmaceutical is administered to the subject prior to the PET data acquisition. The emitted positrons undergo positron/electron annihilation with each such annihilation event generating 511 keV gamma rays travelling in opposite directions, thus defining a line-of-response.

The acquisition and control processors 20, 30 are suitably embodied by a digital processor or controller, or by a combination of digital processors or controllers, operating in combination with suitable electronics, power supplies, and so forth configured to operate the x-ray tube (for CT) and radiation detector arrays, to operate a rotational mechanism that revolves the x-ray tube around the subject within the CT gantry 12, and so forth. The reconstruction processors 22, 32 are suitably embodied by a digital processor or controller, or by a combination of digital processors or controllers, optionally in combination with dedicated reconstruction pipeline hardware embodied, for example, as application-specific integrated circuitry (ASIC) hardware. A user interface, such as an illustrated computer 40, is provided to enable a radiologist or other user to configure, initiate, and monitor CT and PET imaging sessions, and to enable the radiologist or other user to view the resulting CT and/or PET images. The illustrated computer 40 includes a display 42, which may be embodied as a cathode-ray tube (CRT) display, a liquid crystal device (LCD) display, a plasma display, an organic light emitting device (OLED) display, or so forth. The computer 40 also includes a keyboard 44 and a mouse 46 as illustrative input devices; however, additional or other input devices (not shown) may also be included such as a trackpad, a trackball, a touch-sensitive matrix coincident with the display 42 to define a touch-sensitive screen, or so forth. In some embodiments, some user interfacing functionality may be integrated with the CT gantry 12 and/or the PET gantry 14 as a built-in LCD display, built-in keypad, or so forth.

With continuing reference to FIG. 1, the stored CT and PET images acquired from a single subject are preferably spatially registered. In some embodiments, the acquisition of the CT and PET images using a unitary hybrid PET/CT scanner such as the illustrated GEMINI™ PET/CT imaging system 10 is deemed sufficient to ensure spatial registration due to a common coordinate system defined for the CT and PET imaging components of the hybrid system. In other embodiments, the images are relatively spatially registered by a spatial registration module 48, and the one or both images modified by the registration process are stored back into the corresponding image memory 24, 34. The spatial registration module 48 can modify the PET image by rigid shifting and rotation and/or by non-rigid or elastic deformation in order to improve the spatial alignment of the PET image respective to the CT image, and the modified (that is, spatially registered) PET image is stored back into the PET images memory 34. Alternatively, the spatial registration module 48 can modify the CT image by rigid shifting and rotation and/or by non-rigid or elastic deformation in order to improve the spatial alignment of the CT image respective to the PET image, and the modified (that is, spatially registered) CT image is stored back into the CT images memory 24. It is also contemplated to shift, rotate, or deform both the CT image and the PET image to accomplish relative spatial registration. The spatial registration can employ intrinsic anatomical landmarks such as the outer contour of the subject or the contour of an anatomical feature which is visible in both the CT and PET images. Additionally or alternatively, the spatial registration can be based on imaged fiducial markers that are placed on the subject prior to the CT and PET imaging in order to provide spatial registration landmarks. Spatial registration can be used in the context of a hybrid PET/CT system to correct for movement of the subject between the CT and PET image acquisitions. When the multimodality imaging is performed by standalone imaging systems, spatial registration aligns the different and generally unrelated coordinate systems of the standalone imaging modalities.

The CT and PET images, after optional spatial registration, are combined to generate a fused image by an image fusion module 50. The fused image is suitably displayed on the display 42 of the computer 40, or on another suitable display. The illustrated system of FIG. 1 employs an overlay fusion approach in which the CT image serves as an underlay image, and the PET image serves as an overlay image that is color coded in accordance with a current colormap 52 that is derived from a stored colormap 54 by an interactive colormap modifying module 56. The overlay fusion process operates on a per-voxel or per-pixel basis. Defining the underlay image as a first image (typically the CT image), the overlay image as a second image (typically the PET image), denoting a value of a pixel or voxel of the first image as $V_1$, denoting a corresponding color-coded value of a pixel or voxel of the second image as $V_2$, and performing the overlay fusion using a transparency factor or alpha value denoted as $\alpha$, the value of the corresponding pixel or voxel in the fused image is $\alpha V_1 + (1-\alpha)V_2$. As disclosed herein, in for some pixels or voxels the contribution of the overlay is "turned off", for example by setting $\alpha=1$ for those pixels or voxels.

The spatial registration module 48, the image fusion module 50, and the colormap modifying module 56 are suitably embodied by a digital processing device including a suitably programmed digital processor or controller, such as the computer 40. The user-interactive colormap modifying module 56 is configured to receive user input via the mouse 46, keyboard 44, or another user input device, and is configured to communicate information such as a colormap representation to the user via the display 42. Moreover, a storage medium (not illustrated) such as a magnetic disk, optical disk, flash memory, or so forth is suitably encoded with instructions executable by such a processor to embody one or more of the modules 48, 50, 56. Such a storage medium may in some embodiments also store the stored colormap 54.

With continuing reference to FIG. 1 and with further reference to FIG. 2, the stored colormap 54 assigns colors to intensities of an intensity spectrum. FIG. 2 depicts a suitable user interfacing display generated by the interactive colormap modifying module 56 and shown on the display 42, which represents the stored colormap by a colormap representation 60 shown in FIG. 2. The colormap representation 60 shows a horizontal line serving as an abscissa delineating the intensity spectrum, which in the illustrated embodiment ranges from zero intensity to a maximum intensity of 251, so that the intensity spectrum includes 252 discrete intensity values. The maximum intensity of 251 is arbitrary, and in other embodiments other maximum intensity values can be used. For example, in some embodiments the pixel or voxel intensities are represented by eight-bit binary values, for which the maximum intensity is $2^8-1=255$ and the intensity spectrum includes 256 discrete intensity values.

The colormap representation 60 further includes color bins 62 which identify the colors assigned to different pixel or voxel intensities. In the illustrative example, there are 28 color bins 62, all of equal size. Since there are 252 possible intensities in the illustrative intensity spectrum, it follows that each color bin 62 encompasses a range of $252 \div 28 = 9$ intensity values. However, in other contemplated embodiments the color bins may be of different sizes, and/or a different number of color bins may be used, or so forth. In some embodiments, it is contemplated to have the number of color bins equal the number of intensity levels in the intensity spectrum, so that each intensity level of the intensity spectrum is mapped to unique color.

Diagrammatic FIG. 2 is not depicted in color—accordingly, different hatching patterns are used to diagrammatically indicate different colors. The illustrative color spectrum of the colormap of FIG. 2 ranges from blue for the lowest nine intensity values (0-8), through various shades of green, yellow, orange, and red, with the highest nine intensity values (243-251). Intermediate colors (e.g., blue-green shades, green-yellow shades, yellow-orange shades, orange-red shades) are not labelled in FIG. 2. It is to be appreciated that in a color display the color labels shown in FIG. 2 are optionally omitted. Similarly, the abscissa delineating the intensity values 0-251 is also optionally omitted, as the intensity values are implicitly represented by the position of the corresponding color assignment bins 62. Other display variations are also contemplated, such as showing the colormap representation vertically with the color mapping of the lowest intensity at the bottom and the color mapping of the highest intensity at the top, or so forth.

The display generated by the interactive colormap modifying module 50 and shown in FIG. 2 further includes user interfacing instructions. In the illustrative embodiment shown in FIG. 2, these instructions include "Press <F1> to select a color coding modification . . . ". This instructs the user to press the <F1> key to choose to modify the colormap. Upon doing so the user is suitably presented with a list of modification options (not shown). The modification options may include, for example: selecting another stored colormap; modifying colors assigned to the various intensity levels or intensity ranges, for example by using a graphical color-picking application; and selecting a portion of the intensity spectrum to be transparent.

With reference to FIGS. 3-5, some illustrative examples of the latter type of colormap modification, namely selecting a portion of the intensity spectrum to be transparent, are described. FIGS. 3, 4, and 5 depict modified colormap representations 70, 80, 90 that are different user-selected modifications of the stored colormap 54 whose colormap representation 60 is shown in FIG. 2. The colormaps indicated by the respective modified colormap representations 70, 80, 90 are each suitable for use as the current colormap 52 employed by the image fusion module 50 of FIG. 1.

With particular reference to FIG. 3, the modified colormap representation 70 is modified by selecting a lowest range of intensities 72 of the intensity spectrum to be set transparent. The user-interactive display provides the instructions "Move vertical line to select upper transparency bound . . . ". The display of FIG. 3 is suitably generated by the user pressing <F1> at the display shown in FIG. 2, and then selecting an option (not shown) to make a lower region of the intensity spectrum transparent. The "vertical line" reference in the displayed instructions is a dashed vertical line cursor 74 that the user can move left or right using the mouse 46, left- or right-arrow keys of the keyboard 44, or by using another available user input device.

The image fusion module 50 interprets the lowest range of intensities 72 which are selected to be transparent in such a way that the fusion process combines the first (e.g., CT) image and pixels or voxels of the color coded second (e.g., PET) image that are not set to be transparent to generate the fused image. One suitable process is as follows: (1) generate an underlay image as a grayscale representation of the first (CT) image; (2) generate an overlay image as a color coded representation of the second (PET) image, using the colormap of FIG. 3 with pixels or voxels whose intensity value lies in the range of intensities 72 which are selected to be transparent assigned a designated key color; (3) assign the pixel or voxel value $\alpha V_1 + (1-\alpha)V_2$ if $V_2$ is not equal to the key color, otherwise assign the pixel or voxel value $V_1$ (or, equivalently, set $\alpha=1$) if $V_2$ is equal to the key color; and repeat operation (3) for every pixel or voxel of the image. Again, $V_1$ denotes a value of a pixel or voxel of the first (CT) image, $V_2$ denotes a corresponding color-coded value of a pixel or voxel of the second (PET) image; and a is the transparency factor or alpha value.

The key color can be, for example a white color if white is not included in the stored colormap 54, or can be any other color not included in the stored colormap 54, or can be some value that does not denote any real color (that is, a "ficticious" key color). As another approach, the step (2) can generate pixel or voxel values only for those pixels or voxels that are not to be set transparent, and step (3) is modified slightly to assign the pixel or voxel value $\alpha V_1 + (1-\alpha)V_2$ if $V_2$ exists, otherwise assign the pixel or voxel value $V_1$ if $V_2$ does not exist. In this approach, no key color is involved.

The modified colormap of FIG. 3 can be advantageously used in various clinical PET/CT applications. For example, consider an application in which the intensity spectrum maps to a standard uptake value (SUV) range of 0 to 5. That is, using the intensity spectrum of FIGS. 2-5 linearly map 0 to SUV=0 through 251 to SUV=5. Then if the transparency threshold 74 is set to 125 (SUV=2.5) then pixels or voxels whose SUV is less than 2.5 are transparent and appear as grayscale CT values, so as to provide anatomical context. On the other hand, pixels or voxels whose SUV is greater than 2.5 are color coded according to SUV value in the same way as when using the stored colormap 54. Thus, regions of high SUV which are likely to be actively malignant appear in color and are readily discernable by the medical specialist, but the remainder of the CT image is also shown without being obscured by PET image content, so as to provide context. For a given application, such as for $^{18}$F-FDG PET imaging, SUV of 2.5 may be an appropriate threshold that separates certain benign and malignant lesions. However, because the colormap modifying module 56 is user-interactive, the user can actively adjust the transparency threshold 74 based on personal preference, characteristics of the PET image, or other factors. In one suitable approach, the display 42 is divided into a large image window showing the fused PET/CT image, and a smaller control window showing the content of FIG. 3. In this way, the user can adjust the threshold 74 and see the result in the concurrently displayed image window.

With particular reference to FIG. 4, the modified colormap representation 80 is modified by selecting the lowest range of intensities 72 of the intensity spectrum to be set transparent using the vertical line cursor 74, as described previously with reference to FIG. 2, and is further modified by selecting a highest range of intensities 82 of the intensity spectrum to be set transparent using a second vertical line cursor 84. The result is a color-coded intensity range lying between the transparent ranges 72, 82. The user-interactive display of FIG. 4 provides the instructions "Move vertical lines to select color coding range . . . ". The display of FIG. 4 is suitably generated by the user pressing <F1> at the display shown in FIG. 2, and then selecting an option (not shown) to select an intensity range for color coding. The fusion processing for the modified colormap of FIG. 4 is suitably the same as already described for the colormap of FIG. 3, namely color coding the pixels or voxels to be made transparent to a key color and using the per-pixel or per-voxel fusion algorithm: assign the pixel or voxel value $\alpha V_1 + (1-\alpha)V_2$ if $V_2$ is not equal to the key color, otherwise assign the pixel or voxel value $V_1$ (or, equivalently, set $\alpha=1$) if $V_2$ is equal to the key color.

To see how the modified colormap of FIG. 4 can be clinically useful in evaluating PET/CT images, consider again the example in which the colormap corresponds to SUV from 0 to 5. Then, with the colormap of FIG. 4 having the transparency threshold 74 set to 125 (SUV=2.5) and the upper threshold 84 set to 151 (SUV=3.0), pixels or voxels whose SUV values are between 2.5 and 3.0 will be displayed and blended with the underlay (CT) image. Outside the 2.5 to 3 SUV range, the pixels of the overlay (PET) image are 100% transparent so that the CT image in unmodified form. Again, the interactive colormap modifying module 56 can be used by the medical specialist or other user to modify the intensity (or, in this application, SUV) threshold values 74, 84 to suit personal preferences or characteristics of the PET image. By having the upper transparent range 82, regions of high SUV (e.g., SUV>3.0 in the illustrative example) which are of clinical interest are not obscured by color coding.

The effect of the band of color coding defined by the colormap of FIG. 4 is that regions of SUV>2.5 are surrounded by a color-coded contour. With particular reference to FIG. 5, this effect can be extended using the modified colormap whose representation 90 is shown in FIG. 5 to create SUV isocontours. The colormap of FIG. 5 again includes the lowest range of intensities 72 of the intensity spectrum which are to be set transparent as defined by the upper bound vertical line cursor 74. Additional ranges of intensities 92 are spaced apart to define a plurality of color coding bands spaced apart in the intensity spectrum. Each color coding band includes one or more contiguous intensities of the intensity spectrum. In FIG. 5 each color coding band corresponds to one color bin containing nine contiguous intensities—however, it is contemplated for a color coding band to be as small as a single intensity level. In the illustrative user interface display of FIG. 5, the additional spaced apart ranges of intensities 92 are defined with reference to the vertical line cursor 74 which marks the first color coding band, and by an "isobar spacing" parameter 94 which, in FIG. 5, is input numerically. In the specific illustration of FIG. 5, the isobar spacing parameter 94 has a current value of 28, corresponding to four color bins (28÷9 intensities per color bin). In this approach, the color coding bands are spaced apart by equal intervals; however, color coding bands that are spaced apart by non-equal intervals are also contemplated.

If the color coding bands are narrow, then the colors are relatively the same within each band. In illustrative FIG. 5, each color coding band corresponds to a single color bin, and so the color is singular within each color coding band, although including two or more colors in a single color coding band is also contemplated. By adjusting the user inputs 74, 94, the size and number of color coding bands can be adjusted. Hence, different SUV isocontours can be displayed in different colors. The color coding bands map to intensity (or, for this application, SUV) isocontours in the fused image, while all other pixels or voxels are shown in the fused image as CT image pixels or voxels without any content from the PET image. The color contours can, for example, indicate the abruptness or gradualness of SUV transitions at the edges of the tumor, and may also be indicative of regions of rapid angiogenesis or, alternatively, of tissue necrosis.

Although clinical CT/PET is described herein as an illustrative example, the image display techniques disclosed herein are applicable to substantially any type of multimodality imaging, such as SPECT/CT, MR/PET, MR/SPECT, or so forth.

Additionally, it will be appreciated that the color coding techniques disclosed herein for image fusion are also useful in the context of display of a monomodality image. For example, the modified colormap of FIG. 2 can be used for displaying a PET image by itself (without fusion to a CT or other-modality image). In one approach, the PET image serves as both the underlay image displayed in grayscale and as the color coded overlay image. This can be used, for example, to highlight via color coding regions of high SUV. If the colormap of FIG. 4 or of FIG. 5 is used for displaying a PET image alone, then the effect is to highlight by color encirclement such regions of high SUV.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An image display method comprising:
   color coding an overlay image respective to an intensity spectrum using a color map that assigns colors to intensities and that sets a portion of the intensity spectrum to be transparent, the color coding generating a color coded overlay image;
   combining an underlay image and the color coded overlay image to generate a fused image using partial transparency controlled by a transparency factor α for those portions of the overlay image not set to be transparent by the color coding; and
   displaying the fused image on a display;
   wherein the color coding and the combining are performed by a digital processing device.

2. The image display method as set forth in claim 1, wherein the color coding assigns a key color to the portion of the intensity spectrum set to be transparent, and the combining comprises:
   adding pixels or voxels of the color coded overlay image to corresponding pixels or voxels of the underlay image in accordance with the controlling transparency factor α without adding pixels or voxels of the color coded overlay image that are assigned the key color.

3. The image display method as set forth in claim 2, further comprising:
   adjusting the transparency factor α without adjusting the portion of the intensity spectrum set by the color map to be transparent.

4. The image display method as set forth in claim 1, wherein the portion of the intensity spectrum set by the color map to be transparent includes a range of non-zero intensities having a non-zero lowest intensity.

5. The image display method as set forth in claim 4, wherein the range of non-zero intensities further has a highest intensity that is less than a maximum intensity of the intensity spectrum.

6. The image display method as set forth in claim 1, wherein the overlay image is a functional image and the portion of the intensity spectrum set by the color map to be transparent includes a lowest portion of the intensity spectrum, the lowest portion having a highest intensity selected to set as transparent pixels or voxels of the functional overlay image that represent a lower range of standard uptake values (SUV's).

7. The image display method as set forth in claim 1, wherein the portion of the intensity spectrum set by the color map to be transparent includes two or more spaced apart ranges of intensities.

8. The image display method as set forth in claim 1, wherein the portion of the intensity spectrum set by the color map to be transparent includes a first range of intensities and a second range of intensities that are spaced apart in the intensity spectrum.

9. The image display method as set forth in claim 1, wherein the portion of the intensity spectrum set by the color map to be transparent includes a plurality of spaced apart ranges of intensities that define a plurality of color coding bands spaced apart in the intensity spectrum, each color coding band including one or more contiguous intensities of the intensity spectrum.

10. The image display method as set forth in claim 9, wherein the color coding bands are spaced apart in the intensity spectrum by equidistant intervals.

11. The image display method as set forth in claim 1, wherein the underlay image is a computed tomography (CT) image.

12. The image display method as set forth in claim 1, wherein the overlay image is a positron emission tomography (PET) image.

13. An image display system comprising:
   an image generating module configured to generate an image by color coding an input image in accordance with a color map assigning colors to intensities of an intensity spectrum and fusing the color coded image with a second input image;
   a color map modifying module configured to set a portion of the intensity spectrum to be transparent; and
   a display configured to display the generated image;
   wherein the image generating module is configured to fuse the color coded image with the second input image using overlay fusion with the second input image defining an underlay image displayed in grayscale and the color coded image defining an overlay image, the overlay fusion using partial transparency of the color coded overlay image controlled by a transparency factor α except where the color coded overlay image is set to be transparent by the color coding of the overlay image in accordance with the color map.

14. The image display system as set forth in claim 13, further comprising:
   a spatial registration module configured to relatively spatially register the input image and the second input image.

15. The image display system as set forth in claim 13, wherein the overlay fusion comprises assigning the value $\alpha V_1 + (1-\alpha)V_2$ where $V_1$ is the pixel or voxel value of the underlay image and $V_2$ is the pixel or voxel value of the color coded overlay image.

16. The image display system as set forth in claim 13, wherein the color map modifying module is configured to receive a user input selecting the portion of the intensity spectrum that is set to be transparent.

17. The image display system as set forth in claim 13, wherein the color map modifying module is configured to set a plurality of non-contiguous portions of the intensity spectrum to be transparent.

18. The image display system as set forth in claim 13, wherein the color map modifying module is configured to set lower and upper portions of the intensity spectrum to be transparent.

19. The image display system as set forth in claim 13, wherein the color map modifying module is configured to set the portions of the intensity spectrum to be transparent so as to define color coding bands spaced apart in the intensity spectrum, each color coding band including one or more contiguous intensities of the intensity spectrum.

20. A non-transitory storage medium storing instructions executable by a digital processing device to perform a method comprising:
- color coding an overlay image respective to an intensity spectrum using a color map that assigns colors to intensities and that sets a portion of the intensity spectrum to be transparent, the color coding generating a color coded overlay image;
- combining an underlay image and the color coded overlay image to generate a fused image using partial transparency controlled by a transparency factor $\alpha$ for those portions of the overlay image not set to be transparent by the color coding; and
- displaying the fused image on a display.

21. The non-transitory storage medium as set forth in claim 20, wherein the color coding assigns a key color to the portion of the intensity spectrum set to be transparent, and the combining comprises:
- adding pixels or voxels of the color coded overlay image to corresponding pixels or voxels of the underlay image in accordance with the controlling transparency factor $\alpha$ without adding pixels or voxels of the color coded overlay image that are assigned the key color.

22. The non-transitory storage medium as set forth in claim 20, wherein the portion of the intensity spectrum set by the color map to be transparent includes a range of non-zero intensities having a non-zero lowest intensity.

23. The non-transitory storage medium as set forth in claim 22, wherein the range of non-zero intensities further has a highest intensity that is less than a maximum intensity of the intensity spectrum.

24. The non-transitory storage medium as set forth in claim 20, wherein the portion of the intensity spectrum set by the color map to be transparent includes two or more spaced apart ranges of intensities.

25. The non-transitory storage medium as set forth in claim 20, wherein the portion of the intensity spectrum set by the color map to be transparent includes a first range of intensities and a second range of intensities that are spaced apart in the intensity spectrum.

26. The non-transitory storage medium as set forth in claim 20, wherein the portion of the intensity spectrum set by the color map to be transparent includes a plurality of spaced apart ranges of intensities that define a plurality of color coding bands spaced apart in the intensity spectrum, each color coding band including one or more contiguous intensities of the intensity spectrum.

* * * * *